United States Patent
Klausz et al.

(10) Patent No.: US 7,453,982 B1
(45) Date of Patent: Nov. 18, 2008

(54) SYSTEM AND METHOD TO ACQUIRE RADIOLOGICAL IMAGES OF AN IMAGED SUBJECT

(75) Inventors: Remy A. Klausz, Neuilly sur Seine (FR); Alain Rauby, Gif sur Yvette (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/743,902

(22) Filed: May 3, 2007

(51) Int. Cl.
*G01N 23/04* (2006.01)
*H05G 1/02* (2006.01)

(52) U.S. Cl. .......................................... 378/62; 378/197
(58) Field of Classification Search .................... 378/4, 378/15, 19, 37, 62, 64, 98.8, 193, 195, 196, 378/197, 208, 901
See application file for complete search history.

(56) References Cited

U.S. PATENT DOCUMENTS 6,031,888 A * 2/2000 Ivan et al. ..................... 378/20
6,520,677 B2 * 2/2003 Iizuka ........................ 378/209
6,754,297 B2 * 6/2004 James ............................. 378/4
7,139,368 B2 * 11/2006 Kawanabe ................... 378/162

OTHER PUBLICATIONS

GE Healthcare. "Mammography—Senographe DS." http://www.gehealthcare.com/euen/mammography/products/senographe-ds/index.html. Viewed May 3, 2007.

* cited by examiner

*Primary Examiner*—Irakli Kiknadze (57) ABSTRACT

A system to acquire radiological images of an imaged subject is provided. A gantry moves a radiation source and image receptor to multiple positions in relation to an imaged subject. A controller comprises program instructions that include correlating sequence selectors with sequences of acquired images acquired at multiple positions of the gantry, detecting actuation of a first selector correlated to a first sequence, instructing the gantry to position the radiation source and receptor at a first position to acquire a first image in the first sequence, moving the radiation source and receptor while simultaneously detecting actuation of the validation pedal until reaching the first position, acquiring the first image, automatically instructing the gantry to move the radiation source and receptor to a second position to acquire a second image in the first sequence, repeating these steps to acquire the remainder of the images in the first sequence.

17 Claims, 4 Drawing Sheets

SYSTEM AND METHOD TO ACQUIRE RADIOLOGICAL IMAGES OF AN IMAGED SUBJECT

BACKGROUND OF THE INVENTION

The subject matter generally relates to the field of radiological imaging and, more particularly, to a system and method to acquire a desired view of a radiological image.

A certain known technique of radiological imaging is performed with an x-ray imaging system including a mobile arm operable to move a radiation source and image receptor in relation to an imaged subject. Types of control arms include a C-shaped arm or an O-shaped arm.

A certain known type of radiological imaging system is employed in mammography to acquire radiological images of breast tissue. Generally, multiple different views of the breast are desired in diagnostic mammography. Each of the multiple different views generally corresponds to a different position of the X-ray source and the image receiver in relation to the breast tissue. Examples of imaging techniques employed in diagnostic mammography include, cranio-caudal imaging, lateral imaging, and medio-lateral imaging. Cranio-caudal imaging generally includes irradiating the breast tissue from above so as to obtain a view of the breast in the patient's frontal head to foot axis. Lateral imaging generally includes irradiating the breast tissue from the side so as to obtain a view from the gland in an axis transverse to the patient's body. Medio-lateral oblique (MLO) imaging generally includes irradiating the breast tissue at an oblique viewing angle with respect to a reference axis, usually with respect to the patient's frontal head to foot axis.

BRIEF DESCRIPTION OF THE INVENTION

There is a need for a control system to cause continued actuation under the control of an operator to move the mobile arm in support of the radiation source and receiver in relation to the imaged subject. There is also a need to accurately locate the radiation source and receiver at a desired position in relation to the imaged subject without occupying the operator's hands, so as to be available to perform other tasks.

The embodiments of the subject matter described herein address the needs described above.

In accordance with one embodiment, an imaging system operable to acquire radiological images of an imaged subject is provided. The imaging system includes a radiation source operable to transmit radiation toward an image receptor, with the imaged subject located therebetween. The system further includes a gantry operable to move the radiation source and the image receptor to multiple positions with respect to the imaged subject. The system further includes a controller in communication to move the mobile arm. The controller includes a validation pedal, and a processor in communication with a memory. The memory includes a series of program instructions for execution by the processor. The series of program instructions include a) correlating a plurality of sequence selectors with a plurality of sequences of the plurality of positions of the gantry, each of the plurality of sequences representative of a different order of the plurality of positions of the gantry; b) storing a correlation of each of the plurality of sequences in relation to the plurality of sequence selectors in the memory; c) actuating a first sequence selector correlated to a first sequence; d) instructing the gantry to position the radiation source and the image receptor at a first position relative to the imaged subject according to the first sequence automatically in response to step (c); e) stopping the gantry from moving the radiation source and the image receptor with respect to the imaged subject; f) detecting actuation of a validation pedal, and in response ending the step (e) and moving the radiation source and the image receptor to a first position in the first sequence, the validation pedal different from the plurality of sequence selectors; g) moving the gantry to move the radiation source and the image receptor while simultaneously detecting actuation of the validation pedal of step (f) until reaching the first position; h) acquiring a first image at the first position according to the first sequence; i) instructing the gantry to move the radiation and the image receptor to the second position to acquire a second image according to the first sequence, the step (i) initiated automatically in response to step (h) without additional instruction from the operator; and j) repeating steps (d), (e), (f), (g), (h), and (i) to acquire the remainder of the plurality of images according to the one of the plurality of sequences correlated to the one of the plurality of position selectors of step (c).

In accordance with another embodiment, a method to acquire radiological images of an imaged subject with an imaging system is provided. The method comprises the steps of a) storing a plurality of positions of the gantry to move the radiation source and the image receptor with respect to the imaged subject; b) correlating a plurality of sequence selectors with a plurality of sequences of the plurality of positions of the gantry, each of the plurality of sequences representative of a different order of the plurality of positions of the gantry; c) storing a correlation of each of the plurality of sequences in relation to the plurality of sequence selectors in the memory; d) actuating a first sequence selector correlated to a first sequence; e) instructing the gantry to position the radiation source and the image receptor at a first position relative to the imaged subject according to the first sequence automatically in response to step (d); f) stopping the gantry from moving the radiation source and the image receptor with respect to the imaged subject; g) detecting actuation of a validation pedal, and in response ending the step (f) and moving the radiation source and the image receptor to a first position in the first sequence, the validation pedal different from the plurality of sequence selectors; h) moving the gantry to move the radiation source and the image receptor while simultaneously detecting actuation of the validation pedal of step (g) until reaching the first position; i) acquiring a first image at the first position according to the first sequence; j) instructing the gantry to move the radiation and the image receptor to the second position to acquire a second image according to the first sequence, the step (j) initiated automatically in response to step (i) without additional instruction from the operator; and k) repeating steps (e), (f), (g), (h), (i), and (j) to acquire the remainder of the plurality of images according to the one of the plurality of sequences correlated to the one of the plurality of position selectors of step (d).

Embodiments of varying scope are described herein. In addition to the aspects described in this summary, further aspects will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
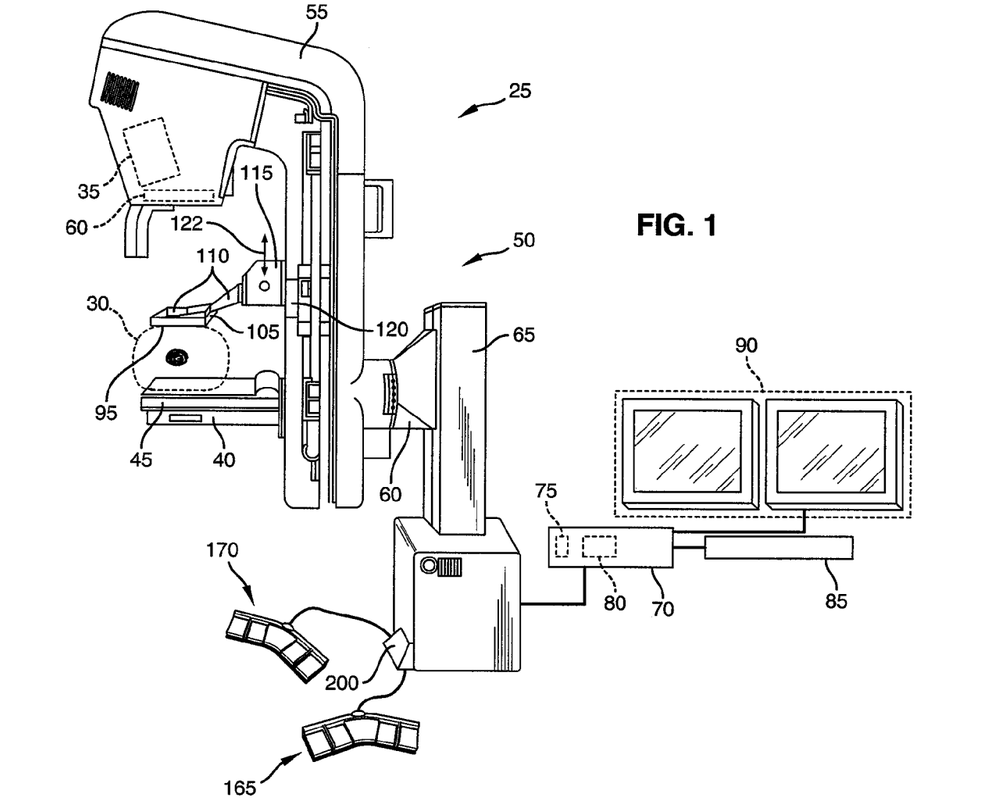
FIG. 1 is a schematic diagram of an embodiment of an imaging system operable to acquire images of an imaged subject from multiple positions.

FIG. 1 illustrates an embodiment of an imaging system 25 operable to acquire multiple different views of radiological images of an imaged subject 30. The illustrated imaging system 25 is configured to acquire diagnostic mammography images of a breast tissue of the imaged subject 30. Yet, the type of imaging system 25 can vary.

The imaging system 25 generally includes a radiation source 35 (e.g., x-rays) in communication with an image receptor 40 in a known manner so as to generate radiological images of the imaged subject 30 located therebetween. Examples of the image receptor 40 include a fluorescent screen, radiographic film, x-ray image intensifier tube, solid state detector, or gaseous detector, which generally transforms incident x-ray photons either into a visible image or into another form which can be made into a visible image by further transformations. The imaging system 25 further includes a breast support plate 45 located to support the breast of the imaged subject 30 between the radiation source 35 and the image receptor 40. In accordance with one embodiment, an upper surface of the image receptor 40 is removably connected in support of the breast support plate 45.

The imaging system 25 also includes a gantry 50 constructed in mobile support of the radiation source 35 and image receptor 40 in relation to the imaged subject 30. The illustrated gantry 50 includes a mobile arm 55 that is generally C-shaped or U-shaped. Yet, it should be understood that the mobile arm 55 could be of other shapes (e.g., circular, etc.). The radiation source 35 and the image receptor 40 are located at opposite ends of the mobile arm 55 so as to acquire radiological images of the imaged subject 30 located therebetween. An embodiment of the mobile arm 55 is generally mounted so as to rotate about an axis 60 orthogonal to a column 65. Examples of the imaging system 25 include the SENOGRAPHE® DS system as manufactured by GENERAL ELECTRIC®, and the MAMMOMAT® system as manufactured by SIEMENS®.

The imaging system 25 also includes a controller 70 connected in communication with the radiation source 35 and image receptor 40. The controller 70 generally includes a processor 75 in communication in a conventional manner with a memory 80. The memory 80 is generally configured to store computer readable program instructions to be executed by the processor 75. The controller 70 is also connected in communication with an input 85 and an output 90. Examples of the input 85 include a keyboard, a touch-screen, mouse device, etc. or combination thereof. Examples of the output 90 include a monitor, a speaker, light-emitting diodes (LEDs), etc. or combination thereof.

The imaging system 25 also includes a rectangular compression plate 95 comprised of an X-ray transparent material, such as polycarbonate. The rectangular compression plate 95 is generally located between the radiation source 35 and the imaged subject 30. A U-shape clamp 100 is secured to a peripheral ledge 105 along the distal edge of the compression plate 95 and over part side edges of the compression plate 95. The clamp 100 is secured to one end of an arm 110. The other end of the arm 110 is secured to a support 115 fixed to a carriage 120. The carriage 120 is operable to move in a direction 122 between the radiation source 35 to the image receptor 40. Thereby, the carriage 120 is operable to move the compression plate 95 between the image receptor 40 and the radiation source 35, along the propagation direction of the X-rays in parallel to the direction 122.

Figure 2:
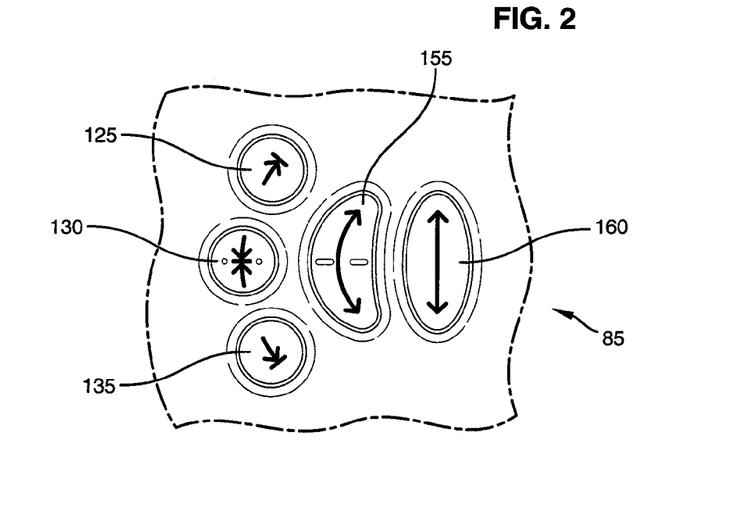
FIG. 2 is a schematic diagram of an embodiment of a controller of the system shown in FIG. 1.

Referring to FIGS. 1 and 2, an embodiment of the input 85 of the controller 70 includes sequence selectors 125, 130 and 135 each corresponding to different sequences of angulations of the gantry 50 and attached radiation source 35 and image receptor 40 relative to the imaged subject 30. According to one embodiment, the sequence selectors 125, 130 and 135 of the controller 70 are finger-operated buttons. Alternatively, the sequence selectors 125, 130, and 135 can include icons on a monitor actuated by a mouse device.

Figure 3:
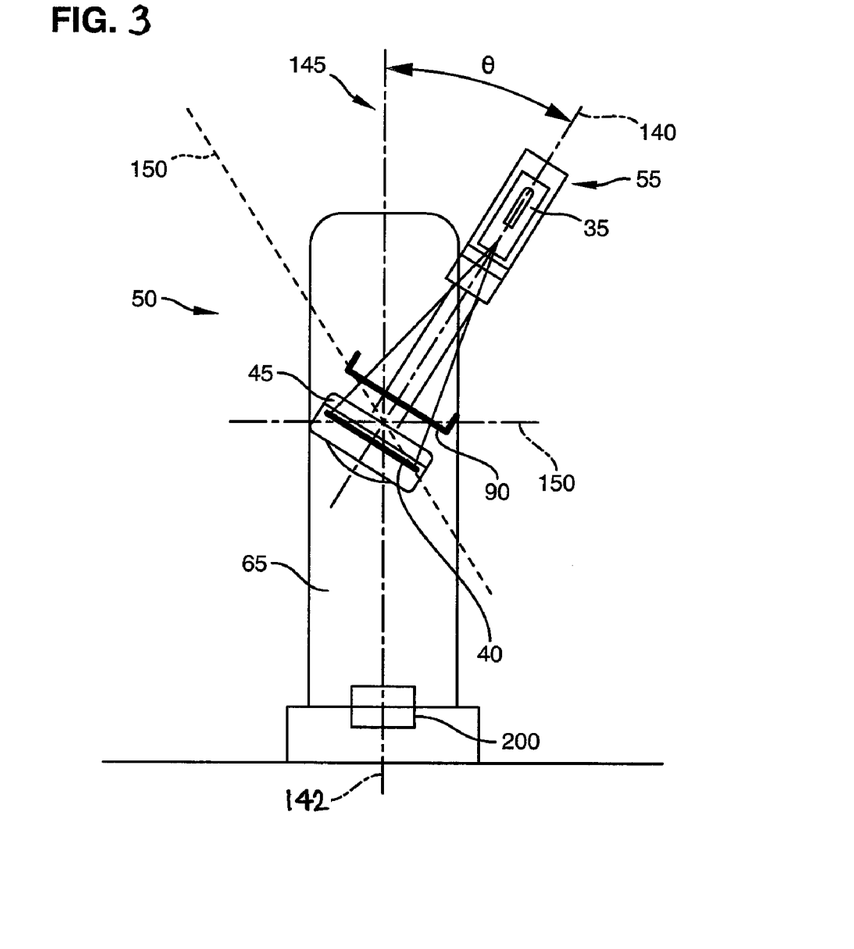
FIG. 3 is a schematic diagram of an embodiment of multiple different angular positions of the gantry and attached source and image receptor of the imaging system of FIG. 1.

Referring to FIG. 3, one embodiment of an angulation or alignment of the gantry 50 and attached radiation source 35 and image receptor 40 includes a first medio-lateral oblique (MLO) alignment position 140. At this position 140, an operator can perform a medio-lateral oblique imaging technique that includes irradiating the breast tissue of the imaged subject 30 at an oblique viewing angle (θ) of about 45° with respect to a vertical axis 142 typically extending through the imaged subject 30. Another embodiment of an angulation or alignment of the gantry 50 includes a cranio-caudal alignment position 145. At this position 145, the radiation source 35 and the image receptor 40 generally coincides with the vertical axis 138 in such a way so that the operator can perform a cranio-caudal imaging technique that includes irradiating the breast of the imaged subject 30 from above so as to obtain a vertically downward view of the imaged subject 30. A third angulation or alignment of the gantry 50 includes a second medio-lateral alignment oblique position 150. At this position 150, the mobile arm 55 of the gantry 50 is generally symmetric relative to the first medio-lateral oblique position 140, the oblique viewing angle of about (45°) in an opposite direction from the vertical axis 138.

Referring to FIGS. 2 and 3, the input 85 of the controller 70 further comprises a fine adjustment selector 155 that is operable to fine adjust an angular or alignment deviation of the mobile arm 55 of the gantry 50 to a desired value generally ranging between 0° (generally coincident with the cranio-caudal angular position 145) and 90° (generally coincident with a horizontal alignment position 158). The input 85 also includes a height push-button 160 that is generally operable to adjust a height of the mobile arm 55 of the gantry 50 in a vertical direction along the column 65 relative to a floor 162.

Figure 4:
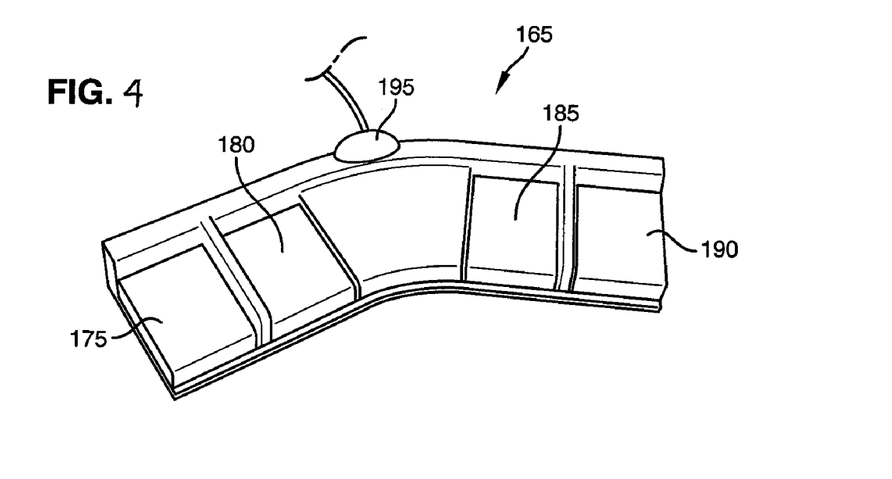
FIG. 4 is a schematic diagram of an embodiment of a validation foot pedal of the system shown in FIG. 1.

Referring back to FIG. 1, the imaging system 20 further includes a first and second foot-operated switch assembly 165 and 170 connected in communication with the controller 70. The first and second foot-operated switch assemblies 165 and 170 are generally located on opposite sides of the imaging system 25. FIG. 4 illustrates an embodiment of the foot-operated switch assembly 165. It should be understood that the foot-operated switch assembly 170 is generally similar in construction.

As illustrated in FIG. 4, the foot-operated switch assembly 165 includes first and second pedals 175 and 180 generally operable to cause the mobile arm 55 of the gantry 50 to move in a vertically downward and upward direction, respectively relative to the floor 162. The foot-operated switch assembly 165 also includes third and fourth pedals 185 and 190 generally operable to cause the compression plate 95 to move in a vertically downward and upward direction, respectively, in the direction 122 relative to the mobile arm 55 of the gantry 50.

The foot-operated switch assembly 165 also includes a foot-operated validation pedal 195 located between the pair of pedals 175 and 180 to control height of the mobile arm 55 and the pair of pedals 185 and 190 to control height of the compression plate 95 along the direction 122 relative to the mobile arm 55. The generally central position of the validation pedal 195 is at an easy reference location relative to the other pedals 175, 180 and pedals 185 and 190.

Having generally provided the above-description of the construction of the imaging system 25, the following is a discussion of a method 200 (See FIG. 5) to acquire multiple different views of radiological images of an imaged subject 30 using the system 25. It should be understood that the following discussion of the method 200 may discuss steps that are optional, and also that method 200 can include additional steps not described herein. Also, it should be understood that the order or sequence of acts or steps of the method 200 can vary. An embodiment of the following description of the acts or steps of the method 200 can be in the form of a series of computer-readable program instructions stored in the memory 80 of the controller 70 for execution by the processor 75.

Figure 5:
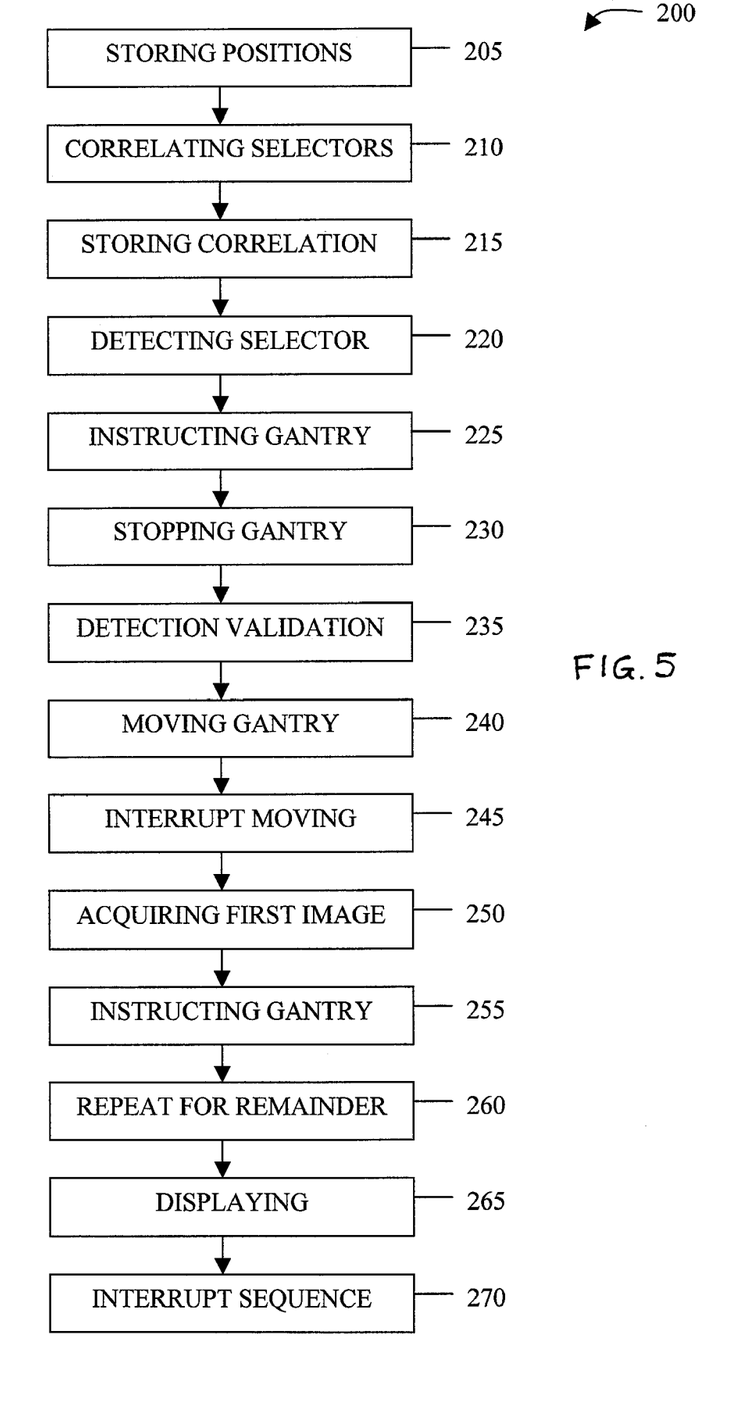
FIG. 5 is a schematic flow diagram of an embodiment of a method to acquire images of an imaged subject from multiple positions with the system of FIG. 1.

Assume the imaged subject 30 is not yet positioned such that the breast tissue is located between the support plate 45 and the compression plate 95. Referring to FIG. 5, step 205 includes storing a series of positions of the gantry 50 to move the radiation source 35 and the image receptor 40 with respect to the imaged subject 30. Step 210 includes correlating each of the series of sequence selectors 125, 130, and 135 with a plurality of sequences of positions 140, 145, and 150 of the gantry 50 and attached radiation source 35 and image receptor 40 relative to the imaged subject 30. Each of the sequences is representative of a different order of the positions 140, 145, and 150 of the gantry 50 to be moved between so as to acquire the images of the sequence. According to one embodiment, the sequence selectors 125, 130, and 135 can be in the form of a user interface of the output 90 and selectable via a mouse device. The sequence selectors 125, 130, and 135 can be in form of a visual interface. Examples of the visual interface include a scroll-down menu, text in graphical representation of a press button, a graphical representation of the corresponding angular position 140, 145, and 150, or similar representation on a monitor and selectable by a click of the mouse or on a touch-screen monitor. The operator can modify the selected angulated position 140, 145, and 150 of the mobile arm 55 by selecting another angular position selector 125, 130 and 135 at any point of the method 200.

Step 215 includes storing a correlation of each of the series of sequences in relation to the sequence selectors 125, 130, and 135 in the memory 80. Step 220 includes actuating a first sequence selector 125 correlated to a first sequence. An embodiment of step 220 includes pressing a finger-operated button. Another embodiment of step 220 includes clicking a mouse at an icon on a monitor.

Step 225 includes instructing (e.g., via a communication signal) the gantry 50 to move the radiation source 35 and image receptor 40 at a first position 140 relative to the imaged subject 30 according to the first sequence in accordance with step 220. Step 225 is performed automatically in response to step 220 without further input from the operator. According to one embodiment in response to step 220, the controller 70 automatically downloads or calls for the data representative of the first position 140 from the memory 80 to instruct the processor 75 to move the gantry 50, without additional instruction or input data from the input 85 or actuation of controls (e.g., sequence selectors 125, 130, and 135) by the operator. Rather, the data for the sequence of positions of the gantry 50 and attached source 35 and image receptor 40 is pre-programmed in the controller 70 to correlate with the actuated sequence selector 125, 130, or 135.

Step 230 includes stopping the gantry 50 from moving the radiation source 35 and the image receptor 40 with respect to the imaged subject 30. Step 235 includes detecting actuation of the validation pedal 195 as described above. In response to detecting actuation of the validation pedal 195, an embodiment of step 235 includes ending step 230 and releasing and moving the gantry 50 and attached radiation source 35 and the image receptor 40 to a first position 140 in the first sequence. The validation pedal 195 is different and independent of the sequence selectors 125, 130, and 135.

Step 240 includes moving the gantry 50 and attached radiation source 35 and image receptor 40 while simultaneously detecting actuation of the validation pedal 195 according to step 235 until reaching the first position 140 in the first sequence. Step 245 includes interrupting step 240 in response to detecting an end of actuation of the validation pedal 195 before the radiation source 35 and image receptor 40 reach the first position 140 in the first sequence. Step 250 includes acquiring a first image with the image receptor 40 at the first position 140 according to the first sequence.

Step 255 includes instructing the gantry 50 to move the radiation source 35 and the image receptor 40 to the second position 145 to acquire a second image according to the first sequence. An embodiment of step 255 is initiated automatically in response to step 250. In a manner similar to step 225, the controller 70 automatically downloads or calls for the data representative of the second position 145 from the memory 80 to instruct the processor 75 to move the gantry 50, without additional instruction or input data from the input 85 or actuation of controls (e.g., sequence selectors 125, 130, and 135) by the operator. Step 260 includes repeating steps (e), (f), (g), (h), 250, and 255 to acquire the remainder of the series of images according to the first sequence correlated to the sequence selector 125, 130, or 135 in accordance with step 220.

Step 265 includes creating a display at the output that is representative of the first position 140 simultaneously during step 225. Another embodiment of step 265 includes creating a display at the output 90 illustrative of the second position 145 simultaneously at step 255 with a display of the first position 140. In response to detecting the radiation source 35 and image receptor 40 reaching the first position 140, another embodiment of step 265 includes creating a display at the output 90 indicative of reaching the first position 140 according to the first sequence.

Step 270 includes detecting actuation of a second sequence selector 130 correlated to a second sequence, and in response, interrupting any one of the respective steps 225, 230, 235, 240, 250, and 255 occurring at the time of actuating the second sequence selector 130, and performing steps 225, 230, 235, 240, 250, and 255 in accordance with the second sequence correlated to the second sequence selector 130.

Although the above description of the method 200 is with respect to initially actuating the first sequence selector 125, it should be understood that the method 200 is applicable in a similar manner to initially actuating either of the other selectors 130 and 135 correlated to second and third sequences, respectively, of image acquisition. It should also be understood that the number of sequences and respective selectors 125, 130, and 135 can vary. Although the above first sequence is described with respect to image acquisition to occur in the sequential order of positions 140, 145, and 150, it should also be understood that the order of the positions 140, 145, and 150 can vary, as well as that the sequences can include positions of the gantry 50 not described herein.

For example, an operator instructs the mobile arm 55 and attached radiation source 35 and image receptor 40 of the imaging system 25 to move to a desired positioned with respect to the imaged subject 30 by pressing one of the series of sequence selectors 125, 130 and 135. Pressing one of the series of sequence selectors 125, 130, 135 can also cause illustration of the selected angulation position 140, 145, or 150 of the mobile arm 55 on the output 90 (e.g., monitor) for viewing by the operator. The output 90 can also include an illustration of the previous angulation position 140, 145, or 150 displacement therefrom of the mobile arm 55 and attached source 35 and image receptor 40 at the time that one of the angular position selectors 125, 130, and 135 was pressed.

Once one of the sequence selectors 125, 130, or 135 is selected or pressed, the operator is free to release the sequence selectors 125, 130, or 135. The mobile arm 55 of the gantry 50 does not start to move toward the selected angular position in accordance with one of the selected sequence selector 125, 130 and 135 until the operator presses the validation pedal 195. Once and as long as the validation pedal 195 is pressed, the mobile arm 55 and attached source 35 and the image receptor 40 will move toward the first position 140, 145 or 150 corresponding to acquisition of the first image in the first sequence correlated to the selected sequence selector 125. The movement of the mobile arm 55 stops if the validation pedal 195 is released, or once the mobile arm 55 is located at the first angular position 140, 145, or 150 in the first sequence. If the validation pedal 195 is released before the mobile arm 55 reaches the first angular position in the first sequence, the mobile arm 55 will not continue to move toward the first position 140, 145, or 150 until the validation pedal 195 is pressed again.

A technical effect of the imaging system 20 described above is operable to free the hands of the operator so as to be available to perform other tasks while the mobile arm 55 of the gantry 50 moves to the angulated positions 140, 145 and 150 of the gantry 50 corresponding to the sequence correlated to the selected sequence selector 125.

Once the mobile arm 55 of the gantry 50 reaches the selected angular position 140, 145, or 150, the controller 70 transmits a signal to generate a display at the output 90 indicative that the movement is complete. Examples of the display include illumination of light, a text message on a monitor, an audible alert, etc. or a combination thereof.

Figure 6:
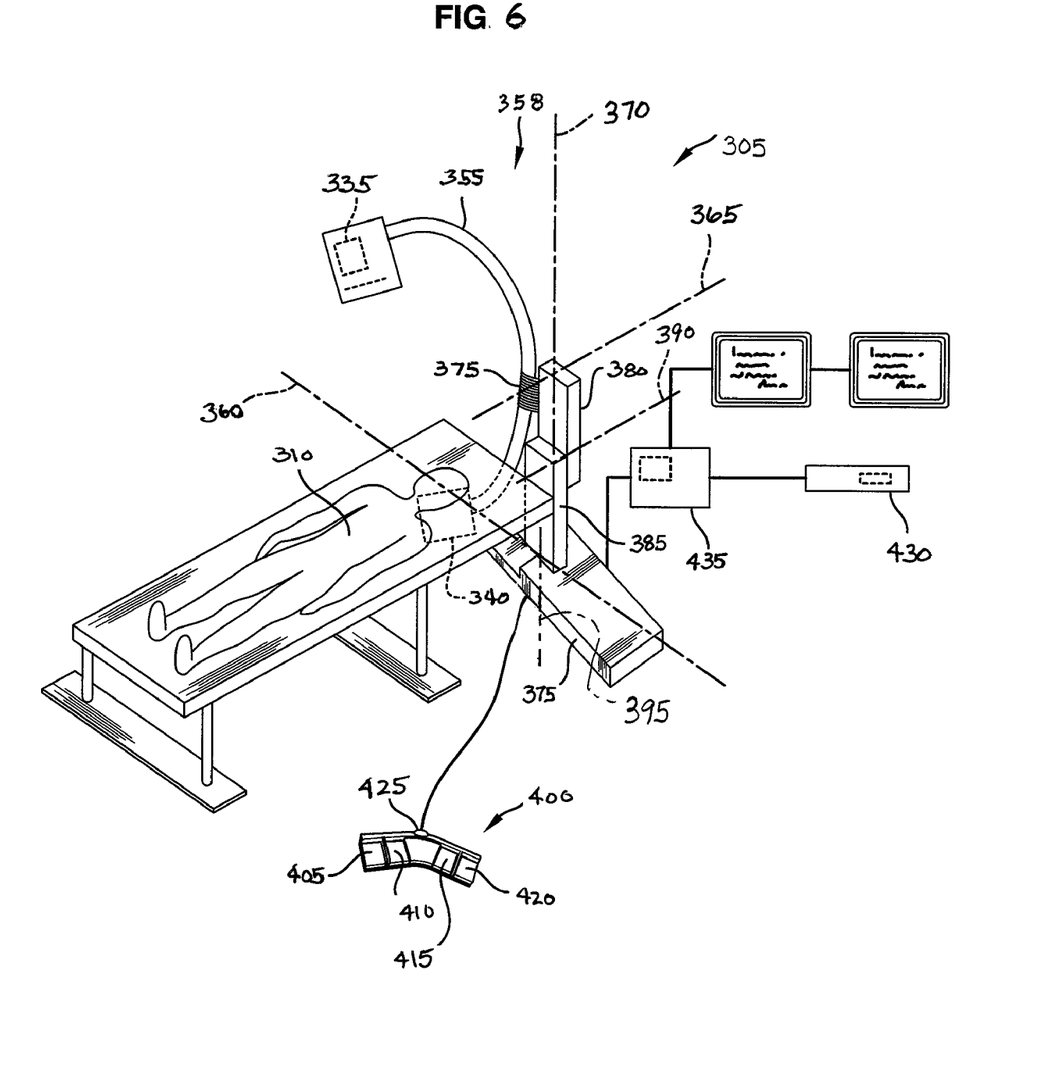
FIG. 6 is a schematic perspective view of another embodiment of an imaging system operable to acquire images of an imaged subject from multiple positions.

FIG. 6 illustrates another embodiment of an imaging system 305, similar to the imaging system 25 described above. The illustrated imaging system 305 is operable to acquire X-ray images of the imaged subject 310. The imaging system 305 generally includes an X-ray source 335 operable to transmit X-rays toward an image receptor 340 (e.g., analog or digital), similar to the source 35 and image receptor 40 described above. The source 335 and image receptor 340 are located at opposed ends of a C-shaped mobile arm 355 of a gantry 358. The C-shaped arm 355 is connected to a carriage 375 so as to slide in a curvilinear manner with respect to the carriage 375 about generally horizontal aligned axis 360. The C-shaped arm 355 is also operable to move with the carriage 375 in a vertical direction along intermediate arm 380. The intermediate arm 380 is pivotally connected at a base arm 385 so as to rotate about generally horizontal-aligned axis 390. The base arm 385 is constructed to rotate about generally vertical-aligned axis 395. The C-shaped arm 315 can therefore pivot about axes 360, 365, 370, 390, and 395. An angulated position of the C-shaped arm 355 can be expressed relative to a reference system defined by a combination of the axes 360, 365, 370, 390 and 395.

The imaging system 305 includes a controller 400 connected in communication with at least one foot-operated switch assembly 402, similar to the foot-operated switch assembly 165 described above. The foot-operated switch assembly 402 includes pedals 405, 410, 415, and 420 and at least one validation pedal 425, similar to the pedals 175, 180, 185, 190 and validation pedal 195 described above.

In a manner similar to the above-description of the operation of the control system 20 in combination with the imaging system 25, the operator selects the desired sequence or order of angular positions of the imaging system 305 relative to the imaged subject by pressing one of the series of sequence selectors 430, similar to the sequence selectors 125, 130, 135 described above. Pressing or actuating the validation pedal 425 causes the gantry 358 and mobile arm 355 to automatically move toward a series of selected angulation positions corresponding to the sequence selector 430 according to program instructions stored in the controller 400.

This written description uses examples to disclose the subject matter described herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of acquiring radiological images with an imaging system, the imaging system including a radiation source operable to direct radiation toward an image receptor and a gantry operable to move the radiation source and the image receptor to multiple positions with respect to the imaged subject, the method comprising the steps of:
   a) storing a plurality of positions of the gantry to move the radiation source and the image receptor with respect to the imaged subject;
   b) correlating a plurality of sequence selectors with a plurality of sequences of the plurality of positions of the gantry, each of the plurality of sequences representative of a different order of the plurality of positions of the gantry;
   c) storing a correlation of each of the plurality of sequences in relation to the plurality of sequence selectors in the memory;
   d) actuating a first sequence selector correlated to a first sequence;
   e) instructing the gantry to position the radiation source and the image receptor at a first position relative to the imaged subject according to the first sequence automatically in response to step (d);

f) stopping the gantry from moving the radiation source and the image receptor with respect to the imaged subject;

g) detecting actuation of a validation pedal, and in response ending the step (f) and moving the radiation source and the image receptor to a first position in the first sequence, the validation pedal different from the plurality of sequence selectors;

h) moving the gantry to move the radiation source and the image receptor while simultaneously detecting actuation of the validation pedal of step (g) until reaching the first position;

i) acquiring a first image at the first position according to the first sequence;

j) instructing the gantry to move the radiation source and the image receptor to the second position to acquire a second image according to the first sequence, the step ( ) initiated automatically in response to step (i) without additional instruction from the operator; and k) repeating steps (e), (f), (g), (h), (i), and (j) to acquire the remainder of the plurality of images according to the one of the plurality of sequences correlated to the one of the plurality of position selectors of step (d).

2. The method according to claim 1, the method further including the step of:

displaying in a first output representative of the first position at step (h).

3. The method according to claim 2, the method further including the step of:

displaying a second output illustrative of the second position at step (j) simultaneously with the first output of the first position.

4. The method according to claim 1, wherein the step of actuating the first sequence selector includes pressing a finger-operated button.

5. The method according to claim 1, wherein the step of actuating the first sequence selector includes clicking a mouse at an icon on a monitor.

6. The method according to claim 1, wherein the validation pedal is foot-operated.

7. The method according to claim 1, wherein in response to the radiation source and the image receptor reaching the first position, the method further includes the step of displaying an output indicative of reaching the first position according to the first sequence.

8. The method according to claim 1, the method further including the steps of:

actuating a second sequence selector correlated to a second sequence; and interrupting any one of the respective steps (e), (f), (g), (h), (i), and (j) occurring at the time of actuating the second sequence selector; performing steps (e), (f), (g), (h), (i), and (j) in accordance to the second sequence.

9. The method according to claim 1, the method further including the step of:

interrupting step (h) in response to detecting an end of actuation of the validation pedal before the radiation source and the image receptor reach the first position.

10. An imaging system operable to acquire radiological images of an imaged subject, comprising:

a radiation source operable to transmit radiation toward an image receptor, with the imaged subject located therebetween;

a gantry operable to move the radiation source and the image receptor to a plurality of positions with respect to the imaged subject; and a controller in communication to move the gantry, the radiation source and the image receptor with respect to the imaged subject, the controller including a plurality of sequence selectors, a validation pedal, and a processor in communication with a memory, the memory including a plurality of program instructions for execution by the processor, the plurality of program instructions representative of the steps of:

a) correlating a plurality of sequence selectors with a plurality of sequences of the plurality of positions of the gantry, each of the plurality of sequences representative of a different order of the plurality of positions of the gantry, b) storing a correlation of each of the plurality of sequences in relation to the plurality of sequence selectors in the memory, c) actuating a first sequence selector correlated to a first sequence, d) instructing the gantry to position the radiation source and the image receptor at a first position relative to the imaged subject according to the first sequence automatically in response to step (c), e) stopping the gantry from moving the radiation source and the image receptor with respect to the imaged subject, f) detecting actuation of a validation pedal, and in response ending the step (e) and moving the radiation source and the image receptor to a first position in the first sequence, the validation pedal different from the plurality of sequence selectors, g) moving the gantry to move the radiation source and the image receptor while simultaneously detecting actuation of the validation pedal of step (f) until reaching the first position, h) acquiring a first image at the first position according to the first sequence, i) instructing the gantry to move the radiation source and the image receptor to the second position to acquire a second image according to the first sequence, the step (i) initiated automatically in response to step (h) without additional instruction from the operator, and j) repeating steps (d), (e), (f), (g), (h), and (i) to acquire the remainder of the plurality of images according to the one of the plurality of sequences correlated to the one of the plurality of position selectors of step (c).

11. The imaging system of claim 10, further including an output with a first display representative of the first position at step (f).

12. The imaging system according to claim 11, the output further including a second display illustrative of the second position at step (i) simultaneously with the first display.

13. The imaging system of claim 10, wherein the validation pedal is foot-operated.

14. The imaging system according to claim 10, wherein the plurality of sequence selectors includes an icon actuable by a click of a computer mouse device.

15. The imaging system according to claim 10, the plurality of program instructions further representative of the steps of:

detecting actuation of a second sequence selector correlated to a second sequence, and interrupting any one of the respective steps (d), (e), (f), (g), (h), and (i) occurring at the time of detecting actuating of the second sequence selector; performing steps (d), (e), (f), (g), (h), and (i) in accordance to the second sequence.

16. The imaging system according to claim 10, the plurality of program instructions further representative of the step of:
  interrupting step (h) in response to detecting an end of detecting actuation of the validation pedal before the radiation source and the image receptor reach the first position.

17. The imaging system according to claim 10, the system further including:
  a compression plate located between the radiation source and the imaged subject, first and second pedals in communication to lower and raise, respectively, a mobile arm of the gantry arm relative to a floor, the mobile arm in mobile support of the radiation source and the image receptor relative to the imaged subject, and third and fourth pedals in communication to lower the compression plate relative to the mobile arm.

\* \* \* \* \*